(12) United States Patent
Gill et al.

(10) Patent No.: US 6,903,555 B2
(45) Date of Patent: Jun. 7, 2005

(54) FLAVOR MONITORING SYSTEM AND METHOD

(75) Inventors: Tejinder K. Gill, Richmond, VA (US); Robert C. Lanier, Jr., Moseley, VA (US); John Dawson, Richmond, VA (US)

(73) Assignee: Philip Moris USA Inc., Richmond, VA (US)

( * ) Notice: Subject to any disclaimer, the term of this patent is extended or adjusted under 35 U.S.C. 154(b) by 94 days.

(21) Appl. No.: 10/293,155

(22) Filed: Nov. 13, 2002

(65) Prior Publication Data

US 2004/0090235 A1 May 13, 2004

(51) Int. Cl.[7] ............ G01N 27/62; A24C 5/34; B31C 13/00
(52) U.S. Cl. ............ 324/464; 131/280; 493/39
(58) Field of Search ............ 324/464, 465–470; 250/335; 73/23.2; 131/280, 900–910, 94, 335–336; 493/39–50

(56) References Cited

U.S. PATENT DOCUMENTS

| | | | |
|---|---|---|---|
| 4,281,671 A | 8/1981 | Byrne et al. ........... 131/335 |
| 4,549,875 A | 10/1985 | Pryor ............... 439/49 |
| 4,607,646 A | * 8/1986 | Lilly, Jr. et al. ........ 131/309 |
| 4,768,526 A | 9/1988 | Pryor ............... 131/335 |
| 4,884,435 A | * 12/1989 | Ehara ............... 73/23.34 |
| 5,561,344 A | * 10/1996 | Hsi ............... 313/494 |
| 5,845,649 A | * 12/1998 | Saito et al. ............ 131/352 |
| 5,892,690 A | * 4/1999 | Boatman et al. ........ 700/276 |
| 6,333,632 B1 | * 12/2001 | Yang et al. ............ 324/464 |

* cited by examiner

*Primary Examiner*—Anjan Deb
*Assistant Examiner*—Jeff Natalini
(74) *Attorney, Agent, or Firm*—Connolly Bove Lodge & Hutz LLP

(57) ABSTRACT

A flavor monitoring system comprises a photo-ionization detector based sensor for measuring the amount of flavor in flavored cigarette filters The sensor has an intake port and an exit port open to the atmosphere. An enclosure with a removable cover is connected to the intake port of the sensor, and the enclosure is constructed and arranged to receive a flavored cigarette filter to be analyzed. The photo-ionization detector based sensor draws a gaseous sample from the flavored filter within the enclosure, ionizes the flavor sample and displays a reading representative of the amount of flavor in the filter. Subsequently the reading may be converted to a flavor amount in milligrams by multiplying the reading by a correlation factor.

2 Claims, 1 Drawing Sheet

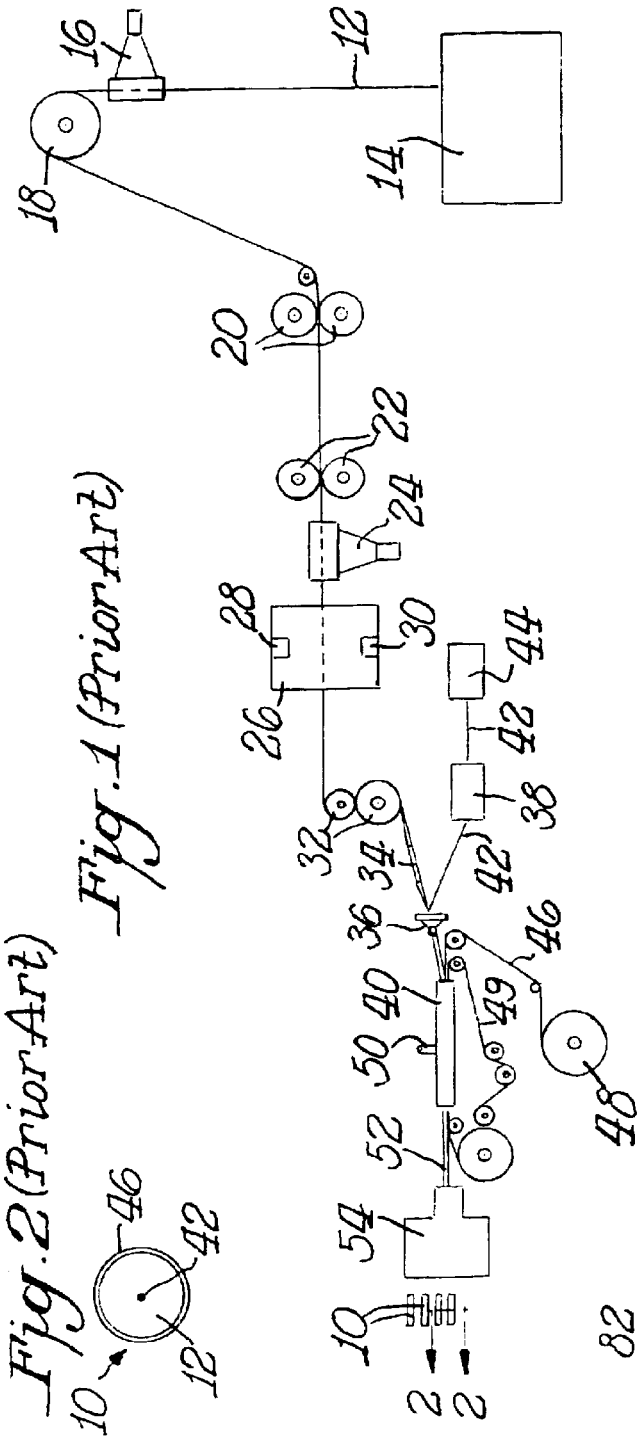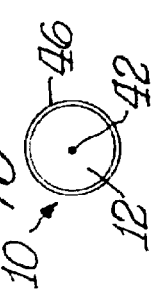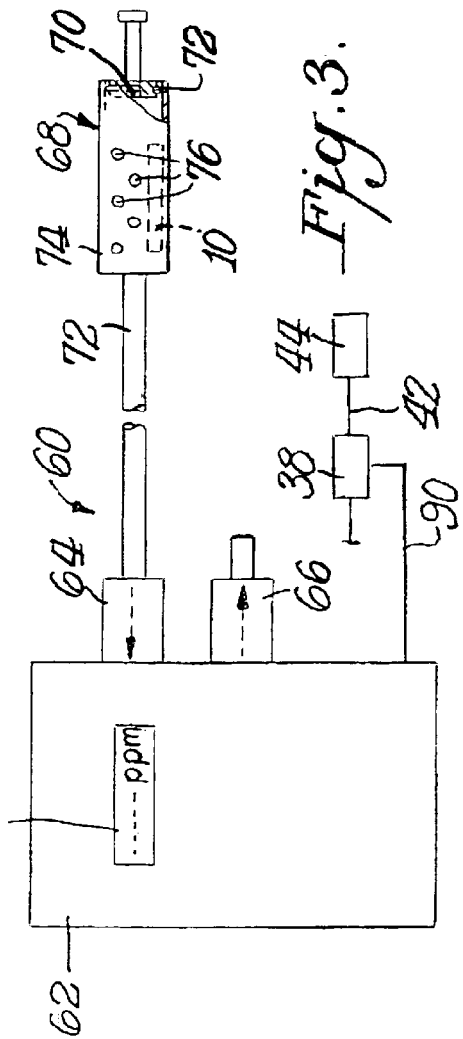

FLAVOR MONITORING SYSTEM AND METHOD

BACKGROUND OF THE INVENTION

The present invention relates to tobacco smoke filters incorporating a smoke-modifying flavor which in use becomes entrained in the smoke passing through the filter, and more particularly to a system for monitoring and adjusting the degree of flavor incorporated in the filter in order to maintain the amount of flavor within prescribed limits.

Flavoring compounds are incorporated into cigarette filters to produce flavored filters that are used to produce flavored cigarettes. It is important to monitor the amount of flavor added to the filter so that the cigarette taste remains generally consistent. In the past, methods such as weight and gas chromatography have been used to determine the amount of volatile flavor compounds in a given flavor substance.

In many instances filter samples are weighed by an operator to determine the amount of volatile flavor compounds that have been added to the filter. Such methods require many filters, usually twenty five to be weighed at one time in order to notice any change in the weight. Results may be adversely effected by moisture or the particular composition of the flavor.

Flavoring liquid used to flavor filters is generally made by dissolving flavoring constituents into a liquid solvent. If the amount of solvent or constituents varies from one batch of flavor to the next, the weight method for determining flavor change is not very accurate. Also, such weight methods cannot detect if only a few filters have non-consistent flavor amounts because the weight method takes the average weight of filters.

Gas chromatography is also used to determine the amount of flavor in cigarette filters. It is a cumbersome process that involves extraction of compounds from the filters and then performing chromatography which involves separation of the flavor composition components. Gas chromatography requires several hours and even days to determine the test results. Also, many volatile components escape during this process. Headspace gas chromatography helps to some extent. Gas chromatography usually requires at least three filters to obtain one reading. Again, variation in one filter would be averaged or masked.

SUMMARY OF THE INVENTION

Accordingly, the primary object of the present invention is obtaining a speedy and reliable measure of the amount of flavor in a flavored cigarette filter or filter component for the purpose of maintaining flavor consistency in high speed filter making machinery.

In accordance with the present invention a flavor monitoring system comprises a photo-ionization detector based sensor for measuring the amount of flavor in flavored filters. The sensor has an intake port and an exit port open to the atmosphere. An enclosure with a removable cover is constructed and arranged to receive a flavored filter, and the enclosure is in fluid communication with the intake port of the sensor. The photo-ionization sensor draws a gaseous sample from a flavored filter within the enclosure, ionizes the flavor sample and displays a reading representative of the amount of flavor. The reading of the sensor is in ppm and that reading may be converted to a flavor amount in milligrams by multiplying the reading by a correlation factor.

The present invention also includes a method for monitoring the flavor amounts in flavored filters.

BRIEF DESCRIPTION OF THE DRAWINGS

Novel features and advantages of the present invention in addition to those mentioned above will become apparent to persons of ordinary skill in the art from a reading of the following detailed description in conjunction with the accompanying drawings wherein similar reference characters refer to similar parts and in which:

FIG. 1 is a schematic side elevational view of a complete apparatus for producing flavored cigarette filters as is well known in the art;

FIG. 2 is a sectional view taken along line 2—2 of FIG. 1 illustrating the cross section of a flavored cigarette filter; and FIG. 3 is a side elevational view of a flavor monitoring system, according to the present invention.

DETAILED DESCRIPTION OF THE INVENTION

Referring in more particularity to the drawings, FIG. 1 illustrates a system for producing individual flavored cigarette filters 10. These filters are subsequently secured to tobacco rods using tipping paper that surrounds the filter and an adjacent portion of the tobacco rod, as is well known. As used herein, the term "filter" means not only a complete cigarette filter ready for assembly to a tobacco rod, but also refers to a filter component of a multiple component filter.

Cellulose acetate tow 12 is drawn from a bale 14 through an air banding jet 16 over a cylindrical guide 18 by rollers 20. Rollers 22 which rotate faster than rollers 20, stretch the tow between themselves and rollers 20. A further air banding jet 24 forms the tow into a band before it passes into a box 26 where it is sprayed with binder such as glyceryl triacetate, for example, by spray guns 28 and 30. The banding jets 16 and 24 are of known form and comprise a narrow slot through which the tow passes. On one side of the slot is a perforate wall which retains the tow while the air impinges upon it. Rollers 32 hold the tow in band form until it passes over an upwardly convex bowed bar 34 upstream of a ring or funnel 36. This shapes the tow reaching funnel 36 into a convenient downwardly concave arch into which is positioned a thread guide mandrel and gives room below the tow 12 for a flavor applicator 38. The flavor applicator 38 is preferably positioned below the tow 12 since if it were situated above the tow, spilled flavor solution might fall onto the tow. The tow is further gathered and condensed into rod form as it enters and passes through a conventional rod-making and wrapping garniture.

The funnel or ring 36 has an internal wall converging downstream. A thread 42 is drawn continuously from a supply 44 through the applicator 38 which applies a flavoring agent to the thread by spraying, for example, or passing the thread through a bath of flavor solution. Upon leaving the applicator 38, the treated thread or flavor element 42 is led directly into engagement with the tow by means of a guide mandrel at a region just upstream of funnel or ring 36, and travels with the tow to and through the garniture 40 to become incorporated in and extend the length of the filter rod produced.

On start up of the apparatus, the tow is threaded through the machine into the garniture, and the free end of flavor element 42 is stuck to the tow upstream of funnel or ring 36. Once the apparatus has been started, the advancing tow continuously entrains the flavor element 42 and draws it continuously from supply 44 through applicator 38 via the guide mandrel. Wrapping paper 46 drawn continuously from reel 48 is fed continuously into the garniture 40, the paper 46 and the tow incorporating flavor element 42 being carried continuously through the garniture by an endless conveyor belt 49.

In the garniture 40, the tow is shaped to rod form, and the paper 46 is wrapped around it and secured with a lapped and stuck seam. Member 50 applies a line of adhesive to one edge of paper 46, before the overlapping edges are brought into engagement. The continuously produced wrapped rod 52 passes to a cutter 54 which severs the rod 54 into individual filter lengths 10.

FIG. 2 is an enlarged cross-sectional view of one of the cigarette filters 10 produced by the apparatus of FIG. 1. Filter 10 comprises a cellulose acetate tow 12 with an approximately centrally positioned flavor element 42 and an outer wrap of paper 46. This filter is similar to the filter produced in accordance with U.S. Pat. No. 4,281,671, incorporated by reference herein in its entirety for all useful purposes.

Flavored cigarette filters 10 may be produced by other procedures that do not include a flavor element. For example, U.S. Pat. Nos. 4,549,875 and 4,768,526, incorporated by reference herein in their entirety for all useful purposes, each disclose the application of controlled amounts of smoke-modifying agents to the interior regions of a cellulose acetate tow during the filter making process. In this regard, a centrally positioned nozzle enveloped by the tow in an encircling manner applies the smoke-modifying agent to the interior regions the filter being produced.

Other procedures may also be utilized for producing flavored cigarette filters such as spraying smoke-modifying agents onto exterior portions of filter tow material during filter production or by applying such agent after the tow is formed into its rod-like shape.

Still other procedures may be used such as drawing the tow material through a bath of smoke-modifying agent.

FIG. 3 shows a flavor monitoring system 60, according to the present invention. System 60 includes a flavor sensor 62 having intake and exit ports, 64 and 66, respectively. An enclosure 68 with a removable cover 70 is arranged to receive a flavored filter 10 to be analyzed. The enclosure 68 is in fluid communication with intake port 64 via a passageway in the form of tubing 72. Enclosure 68 is generally in the form of a syringe that includes a body portion 74 with air vent openings 76. The vent openings are approximately 2 mm in diameter and spaced about 10 mm from each other. Body portion 74 may be constructed from any suitable material including plastic.

In operation, a cigarette filter 10 is placed into the interior of the enclosure 68 and cover 70 is then placed over the open end of the enclosure. A seal 72 on the cover engages the interior of the enclosure to provide a tight fit. The sensor is then energized and air is drawn into the sensor through the vent openings 76. The air flow pulls the volatile flavors from the cigarette filter 10 and these volatiles travel through the tubing 72 to the intake port 64 of the sensor. The flavor quantity is sensed and a reading is displayed on screen 82 in about 30 seconds, as described more fully below.

Sensor 62 is a photo-ionization detector based sensor used to measure the flavor amount in flavored filters 10. In one example the flavor sensor is used at a lamp setting of 10.6 electron volts (eV). This setting may be varied as needed based on the ionization potential of the flavor components.

A gaseous sample from a filter 10 within the enclosure is ionized and the signal is converted into current. The current is then amplified and displayed as a reading on the sensor screen 82. The reading may be displayed in any desired units, including, but not limited to, parts per million (ppm). Flavor sensor 62 has a pump built into it that constantly draws in air. The outlet 66 of the pump is open to the atmosphere. An ultraviolet lamp inside the sensor 62 breaks down the chemical compounds of the gaseous sample from filter 10 into positive and negative ions, and the sensor measures the charge of the ionized gas and converts the signal into current. This value is displayed as ppm on the sensor screen 82.

After the filter is tested for flavor amount the cover 70 is removed from the enclosure 68 and the filter 10 is removed. The sensor goes back to 0 ppm and is ready to read another sample.

Initially a correlation is done between gas chromatography readings and flavor sensor readings and a correlation factor is determined. This correlation factor is used to convert the flavor sensor ppm into the flavor amount in milligrams as measured by gas chromatography.

Placing the flavored filter within the enclosure 68 is an important feature of the present invention in obtaining reliable results. Simply holding the filter near the intake port of the sensor was found to be unreliable.

The flavor sensor 62 is a quick, non-destructive, cost-effective and an easy way of monitoring the flavor level in the filters 10. Gas chromatography analysis takes several hours and then days thereafter to obtain results. On the other hand, flavor sensor 62 quickly provides a check of flavor amount in a manufacturing environment for quality purposes. If the flavor quantity or strength is not consistent within a small batch of filters, there is a better chance of determining this variation with the flavor sensor 62 compared to weight measurement methods or gas chromatography methods because the flavor sensor reads the flavor amount in one filter.

Another disadvantage of gas chromatography is that the samples must be collected in jars. The jars must be made airtight and then submitted for gas chromatography analysis. On the other hand, flavor sensor 62 gives the flavor reading in about 30 seconds and is very easy to use.

Flavor sensor 62 may be used in combination with a programmable logic controller for on-line flavor monitoring. The filter making machinery of FIG. 1 may be programmed to stop if the flavor level in the filter 10 is above or below an acceptable window for flavor amount. Moreover, the flavor application 38 functions to provide flavor to element 42 based upon the speed of the filter making machinery. When the machinery runs at a lower speed, the flavor application rate is less when compared to higher machinery speed when the flavor application rate is higher. These variables produce generally consistent flavor amounts of approximately 4 mg per 8 mm filter length at all times. The flavor sensor 62 may be adapted to continuously monitor the flavor amount of the out coming filters, and stop the filter making machinery when the flavor amount is out of acceptable limits.

Cigarette filters produced by filter making machinery are often randomly sampled for circumference, resistance-to-draw, and other physical characteristics. Automated machines may be used for such sampling, and flavor sensor 62 may be incorporated in that machinery. FIG. 3 diagrammatically illustrates adjustment of the flavor applied at applicator 38 to thread 42 in response to the actual flavor determined by flavor sensor 62 in order to maintain the amount of flavor within prescribed limits. A line 90 interconnects the flavor sensor 62 with the flavor applicator 38.

It should be understood that the above detailed description while indicating preferred embodiments of the invention, are given by way of illustration only, since various changes and modifications within the spirit and scope of the invention will become apparent to those skilled in the art from the detailed description. For example, other forms of enclosures may be used for placement of the filter being tested.

What is claimed is:

1. A method for monitoring and adjusting flavor amounts in a flavored filter comprising the steps of:

placing a flavored filter within an enclosure;

connecting the enclosure to an intake port of a photo-ionization sensor to provide fluid communication between the enclosure and the sensor;

venting the photo-ionization sensor to the atmosphere through an exit port on the sensor;

drawing a gaseous sample from a flavored filter within the enclosure and delivering the sample to the photo-ionization sensor;

ionizing the sample in the sensor;

displaying a reading representative of the flavor amount in the filter; and adjusting responsive to the representative reading the degree of flavor incorporated in the filter in order to maintain the amount of flavor within prescribed units.

2. A method as in claim 1, including the further steps of multiplying the reading representation of the flavor amount by a correlation factor to produce a flavor amount reading in milligrams.

* * * * *